US010710279B2

United States Patent
Deshpande

(10) Patent No.: US 10,710,279 B2
(45) Date of Patent: *Jul. 14, 2020

(54) SYSTEMS AND METHODS FOR MAKING DUST AGENT FREE VULCANIZED RUBBER PRODUCTS

(71) Applicant: Garware Bestretch Limited, Pune (IN)

(72) Inventor: Makarand Deshpande, Aurangabad (IN)

(73) Assignee: Garware Bestretch Limited, Pune (IN)

( * ) Notice: Subject to any disclaimer, the term of this patent is extended or adjusted under 35 U.S.C. 154(b) by 0 days.

This patent is subject to a terminal disclaimer.

(21) Appl. No.: 16/676,626

(22) Filed: Nov. 7, 2019

(65) Prior Publication Data

US 2020/0180192 A1  Jun. 11, 2020

Related U.S. Application Data

(63) Continuation of application No. 16/261,629, filed on Jan. 30, 2019.

(30) Foreign Application Priority Data

Dec. 6, 2018  (IN) .............................. 201821046153

(51) Int. Cl.
| | | |
|---|---|---|
| B29C 37/00 | (2006.01) | |
| B29C 43/24 | (2006.01) | |
| B29C 43/46 | (2006.01) | |
| B29C 43/52 | (2006.01) | |
| B29K 21/00 | (2006.01) | |

(Continued)

(52) U.S. Cl.
CPC ........ B29C 37/0075 (2013.01); A61B 17/132 (2013.01); B29C 43/24 (2013.01); B29C 43/46 (2013.01); B29C 43/52 (2013.01); *B29K 2021/00* (2013.01); *B29L 2031/753* (2013.01)

(58) Field of Classification Search
CPC ..... B29C 37/0075; B29C 43/24; B29C 43/28; B29C 43/46; B29C 43/52; B29L 2031/753; A61B 17/132; A61B 17/1322
See application file for complete search history.

(56) References Cited

U.S. PATENT DOCUMENTS 2,057,701 A * 10/1936 Emery .................... B29C 67/24
428/193
2,067,667 A *  1/1937 Keller .................... B29C 33/66
206/412

(Continued)

FOREIGN PATENT DOCUMENTS

EP         2250992 A1    11/2010
JP        09-234737   *  9/1997

*Primary Examiner* — Jeffrey M Wollschlager
(74) *Attorney, Agent, or Firm* — Dunkiel Saunders Elliott Raubvogel & Hand; Shawn Gordon

(57) ABSTRACT

Processes, and systems for making a substantially smooth surfaced, dust agent free rubber or similar sheet product, are disclosed. To create the dust agent free sheet, a low-shrinkage thermoplastic textile fiber separator is inserted between layers of a calendered sheet so as to be able to separate layers of the sheeting after vulcanization. The use of the separator replaces the use of talc or dust that is commonly used to separate layers of sheeting during or after the calendering process and prior to a heating or vulcanization process.

1 Claim, 3 Drawing Sheets

(51) Int. Cl.
*B29L 31/00* (2006.01)
*A61B 17/132* (2006.01)

(56) References Cited

U.S. PATENT DOCUMENTS

| | | | | |
|---|---|---|---|---|
| 2,391,986 | A | * | 1/1946 | Leach ................ B29C 37/0075 428/339 |
| 2,436,446 | A | | 2/1948 | Nichols et al. |
| 2,639,249 | A | * | 5/1953 | Gurin ................ B29C 33/62 442/260 |
| 2,656,292 | A | * | 10/1953 | Hoover ................ B29C 33/62 442/65 |
| 2,703,436 | A | * | 3/1955 | Rhee ................ B29C 35/0227 264/491 |
| 3,121,912 | A | * | 2/1964 | Dieckmann ........... B29C 37/006 425/371 |
| 3,491,186 | A | * | 1/1970 | Rainar ................ B29C 35/02 264/295 |
| 4,017,654 | A | * | 4/1977 | Evans ................ B29C 35/02 428/40.3 |
| 4,039,609 | A | | 8/1977 | Thiel et al. |
| 4,435,180 | A | * | 3/1984 | Leeper ................ A61K 9/7053 2/901 |
| 4,731,266 | A | | 3/1988 | Bonnebat et al. |
| 4,744,851 | A | * | 5/1988 | Lorenz ................ B29C 33/68 156/247 |
| 4,923,647 | A | | 5/1990 | Tatai et al. |
| 5,169,566 | A | | 12/1992 | Stucky et al. |
| 5,187,005 | A | | 2/1993 | Stahle et al. |
| 5,380,180 | A | | 1/1995 | Lamb, Sr. |
| 5,690,528 | A | * | 11/1997 | Kelley ................ B32B 25/10 442/260 |
| 5,786,058 | A | | 7/1998 | Megchelsen et al. |
| 5,941,475 | A | * | 8/1999 | Gentry, Jr. ............ B65H 19/30 242/533.8 |
| 6,120,887 | A | | 9/2000 | Werenicz et al. |
| 6,136,121 | A | | 10/2000 | Jones et al. |
| 6,689,248 | B1 | * | 2/2004 | Stahr ................ B29C 43/24 156/242 |
| 6,742,472 | B1 | | 6/2004 | Shigyo |
| 7,094,456 | B1 | * | 8/2006 | Vargo ................ B32B 3/10 206/412 |
| 7,341,785 | B2 | | 3/2008 | Kia et al. |
| 7,452,832 | B2 | | 11/2008 | Bansal et al. |
| 8,034,729 | B2 | | 10/2011 | Yoshida et al. |
| 8,377,528 | B2 | | 2/2013 | Kyle et al. |
| 8,381,536 | B2 | | 2/2013 | Nhan et al. |
| 9,062,395 | B2 | * | 6/2015 | Takedomi ................ D03D 1/00 |
| 9,855,686 | B2 | | 1/2018 | Grosz |
| 10,221,290 | B2 | | 3/2019 | Wang et al. |
| 2003/0195284 | A1 | | 10/2003 | Paik et al. |
| 2015/0223552 | A1 | | 8/2015 | Love et al. |
| 2016/0002929 | A1 | * | 1/2016 | Wang ................ E04D 5/10 264/294 |
| 2016/0319090 | A1 | * | 11/2016 | Wang ................ C09D 121/00 |
| 2017/0081802 | A1 | | 3/2017 | Jaakkola et al. |

\* cited by examiner

SYSTEMS AND METHODS FOR MAKING DUST AGENT FREE VULCANIZED RUBBER PRODUCTS

FIELD OF THE INVENTION

The present invention generally relates to rubber processing. In particular, the present invention is directed to Systems and Methods for making Dust Agent Free Vulcanized Rubber Products in sheet form.

BACKGROUND

Esmark (or Esmarch) bandages are used by the medical industry for various purposes, such as "bloodless surgery". These bandages are made from vulcanized rubber sheeting, which in their un-vulcanized form are naturally tacky. For medical purposes, these bandages are desirably substantially smooth, which heretofore has required various other dusting agents like calcium and/or magnesium silicate (commonly referred to as talc), diatomaceous earth, starch, etc. to be used as separating agents during the calendering and vulcanization processes so as to prevent adjacent layers of the un-vulcanized rubber sheeting from sticking to each other. However, the use of dusting agents with rubberized or thermoplastic bandages are not appropriate for all surgical settings and, while various so-called "talc free" or "dust free" bandages have entered the marketplace, in actuality none of them are truly talc and/or dust free and substantially smooth—instead, if they are dust agent and/or talc free the sheets have raised textures that facilitate separation of the sheets.

SUMMARY

In a first aspect, a process for the manufacture of a substantially smooth, dust free, rubber sheet is described, the process comprising calendering a rubber material into a rubber sheet; combining the rubber sheet on a drum with a separator without the use of any dusting agent, wherein the separator is a tightly weaved, low shrinkage, thermoplastic textile; heating the combined rubber sheet and separator so as to vulcanize the rubber sheet; and separating the vulcanized rubber sheet from the separator.

In another aspect, a substantially smooth, dust free, sheet for production of medical bandages is described, the sheet being prepared by a process comprising the steps of: calendering a material into a sheet of a predetermined thickness; combining the sheet on a drum with a separator without the use of any dusting agent via a separation system, wherein the separator is a tightly weaved, low shrinkage, thermoplastic textile, and wherein the separation system is configured to provide the separator to the drum for combination with the sheet and to remove the separator from the drum at a later time: heating the combined sheet and separator; and separating the sheet from the separator via the separation system.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

DETAILED DESCRIPTION

The system disclosed herein provides a substantially smooth surfaced, dust-free rubber sheet product suitable for use in the medical industry. In certain embodiments, the system includes a low-shrinkage thermoplastic textile fiber separator (hereafter, the "separator") sheet so as to separate layers of rubber sheeting that would otherwise stick together. The use of the separator replaces the use of talc or dust that is commonly used to separate layers of rubber sheeting during or after the calendering process and prior to the vulcanization process (after vulcanization, the rubber is no longer naturally tacky). In certain embodiments the separator is constructed using a weave of at least 109×76 threads/square inch so as to leave no, or a very limited, impression on the material to be separated. In an embodiment, the separator is thermally stabilized prior to use with the system. In certain embodiments, the separator is treated with a silicone, such as, but not limited to, polysiloxanes or polydimethylsiloxanes prior to use with the system.

At a high level, the calendering process forces softened un-vulcanized rubber into the center of counter-rotating rollers. Rollers compress the material and the overall thickness of the product is determined by the gap distance between rollers, which can be adjusted to provide varying product thicknesses. Once the material passes through cooling rollers, it must be vulcanized. Vulcanization, generally, takes place in hot air or steam ovens or rotocure at specified time, temperature, and pressure, and may include various chemicals, such as, but not limited to sulfur compounds. For example, vulcanization can occur in a hot air oven over a given duration, such as for 4 hours, at 140 to 150° C. Although the system and process described herein is focused on the processing of rubber (both natural and synthetic), embodiments of the system and process can be readily adapted to be used with other materials, e.g., thermoplastics, that have a tendency to stick to itself during the processing of the material and thus heretofore have required the use of dust agents or textured treatments to allow for separation of the material.

Figure 1:
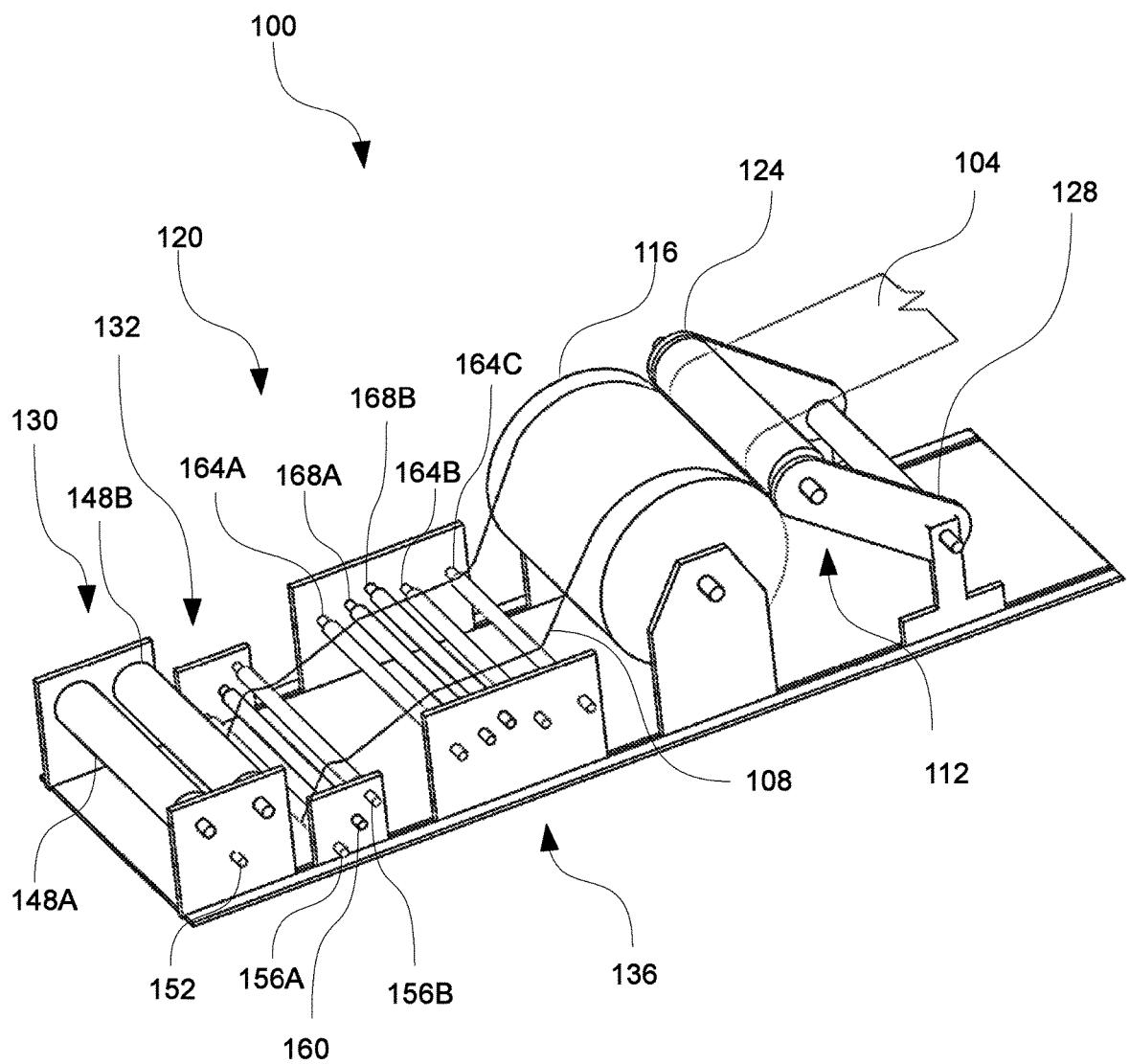
FIG. 1 is a perspective view of a rubber processing system according to an embodiment of the present invention.
Figure 2:
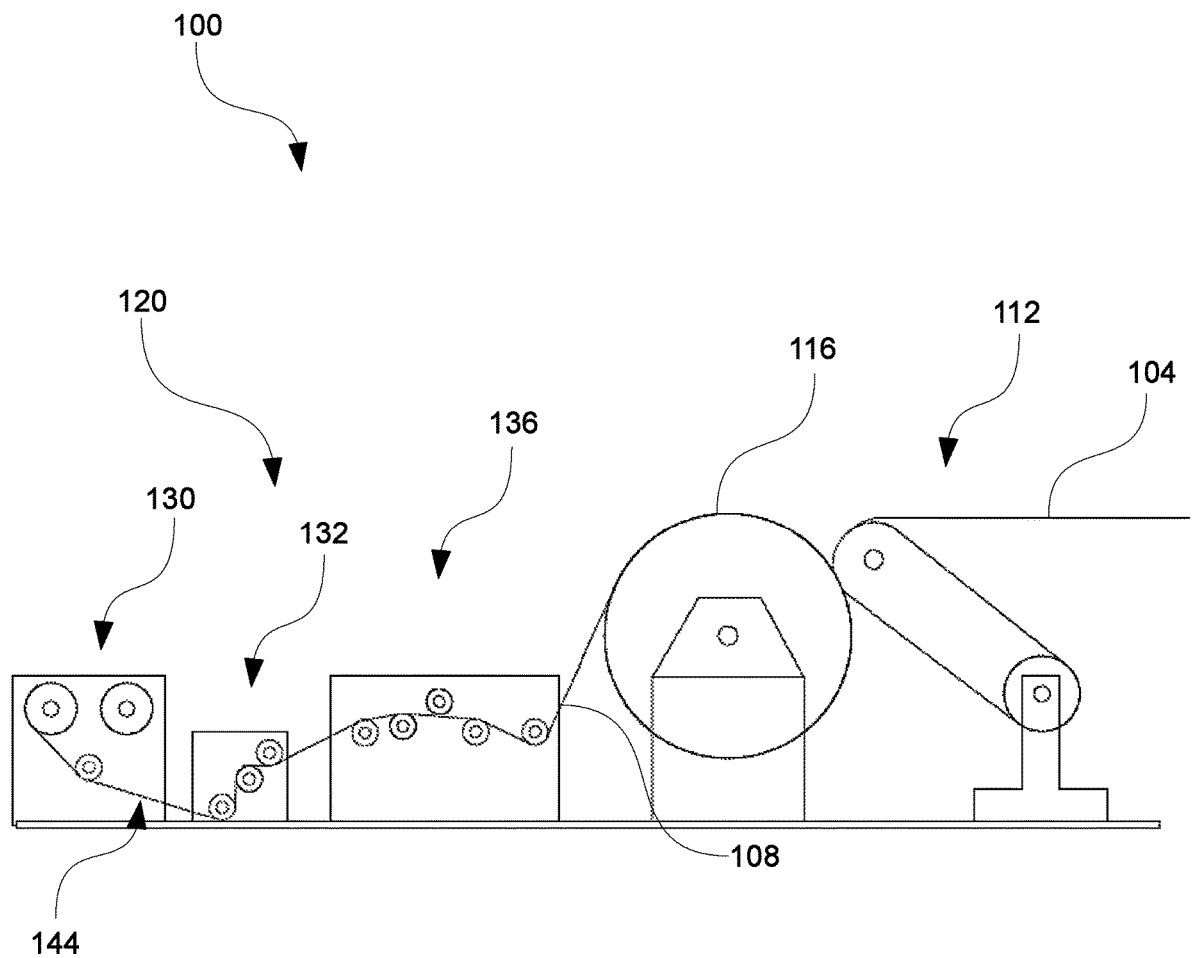
FIG. 2 is a side plan view of the rubber processing system according to an embodiment of the present invention.

Turning now to the figures, and particularly with reference to FIGS. 1 and 2, there is shown a system 100 according to an embodiment of the present disclosure. The system shown in FIGS. 1 and 2 are the same and thus not all element numbers have been reproduced on FIG. 2 to allow for clarity. System 100, at a high level, merges a calenderized rubber sheet 104 with a separator 108 before or during the vulcanization process so as to keep the sheets of calendarized rubber from sticking to each other. Separator 108 can then, when no longer needed, be separated from rubber sheet 104 and reused. As shown in FIGS. 1 and 2, system 100 can include a take-up system 112, a drum 116, and a separator system 120.

Take-up system 112 receives rubber sheet 104 (typically from a calendering system (not shown)) and facilitates its collection onto drum 116. In an embodiment, take-up system 112 includes at least one take-up roller 124 which is attached to a pivot arm 128. In operation, take-up system 112 maintains tension on rubber sheet 104 coming from the calendering system and also the positioning of the calenderized rubber sheet on drum 116.

Drum 116 rotates so as to simultaneously collect rubber sheet 104 as well as separator 108.

Separator system 120 provides separator 108 to be wound (and potentially unwound) with rubber sheet 104. In an embodiment, and as shown in FIGS. 1 and 2, separator system 120 includes a fabric release unit 130, a tensioning system 132, and a guidance system 136, each of which serve to prepare and guide separator 108 on a path 144 (shown in FIG. 2) to drum 116. As shown in the figures, path 144 begins at fabric release unit 130 and ends at drum 116.

Fabric release unit 130 stores and releases rolls of separator 108. In an embodiment, fabric release unit 130 includes a plurality of fabric rollers 148 (148A and B) and at least one idler roller 152. Fabric roller can be configured to hold rolls of separator 108. Idler roller 152 guides separator 108 to tensioning system 132.

Tensioning system 13 provides consistent tension on separator 108 as it travels to drum 116. In an embodiment, tensioning system 132 includes a plurality of idler rollers 156 (156A and 156B) and a load cell roller 160. Load cell roller 160 can provide a signal, representative of a tension. In an embodiment one or more of the rollers that are part of tensioning system 132 can be adjusted to alter the tension on separator 108. The load measured by load cell roller 160 should not preferably exceed 200 N.

Guidance system 136 is designed and configured to ensure crease free application of the separator 108. Guidance system 136 includes a plurality of idler rollers 164 (idler rollers 164A, B, and C) and a plurality of spiral rollers 168 (spiral rollers 168A and B), which work cooperatively to maintain the position of separator 108 relative to drum 116 so that the separator is joined to rubber sheet 104 without creases in the separator. In certainly embodiments, guidance system 136 may also knock free particles and debris from separator 108 before it makes contact with calenderized rubber sheet 104 (which, as a naturally tacking substance will undesirably tend to attract debris and particulate matter). Spiral rollers 168 can be configured to "brush" off particulates and debris as separator 108 makes contact with the spiral ribs that are on each of the spiral rollers. Idler rollers 164 are positioned so as to ensure contact between separator 108 and each of spiral rollers 168.

Path 144, based on the embodiment of separator system 120, is best seen in FIG. 2. As shown, separator 108 is unspooled from one of fabric rollers 148 and passes under idler roller 152 and idler roller 156A, then over load cell roller 160, then under idler roller 156B to guidance system 136. Separator 108 then passes over idler roller 164A, over spiral roller 168A, under spiral roller 168B, over idler roller 164B, and under idler roller 164C, before mating up with calenderized rubber sheet 104 at drum 116.

Separator 108, at a high level, has low shrinkage and is weaved into a very tight pattern such that no impression is imparted to rubber sheet 104 when the two are mated together on drum 116. Separator 108 is also preferably easily released from rubber sheet 104 after vulcanization and is durable enough to be reused. In an embodiment, separator 108 is a low-shrinkage thermoplastic having a shrinkage ratio of less than 1.5. In an embodiment, separator 108 is a low-shrinkage thermoplastic textile fiber such as, but not limited to, nylon, polyester, and nylon 6/6. Separator 108 is preferably thermally stabilized prior to mating with rubber sheet 104. Thermally stabilizing separator 108 reduces the probability of additional shrinkage occurring during the vulcanization process, which applies heat to drum 116. If additional shrinkage occurred during vulcanization, the substantially smooth surface of the rubber sheet 104 may be compromised. In an embodiment, separator 108 is heated to a temperature that is greater than the vulcanization temperature. In an embodiment, separator 108 is heated to a temperature of above 350° F. Separator 108 is preferably readily detachable from rubber sheet 104 after vulcanization and is reusable. In an embodiment separator 108 is chemically treated prior to thermally stabilizing the separator. In this embodiment, the chemical used to treat separator 108 improves the releasability of the separator from rubber sheet 104 and extends the useful life of the separator. In an embodiment, separator 108 is treated with silicones, such as but not limited to polysiloxanes or polydimethylsiloxanes. In an embodiment, after being emulsified with silicones, separator 108 is heat treated.

Separator 108 imparts little to no impression on calenderized rubber sheet 104 when layered on drum 116, in an embodiment, separator 108 is weaved in such a way so as to maintain a substantially smooth surface on calenderized rubber sheet 104. A substantially smooth surface is a surface whereby little to no impression is made on the rubber sheet 104 by virtue of the use of separator 108. In an embodiment, separator 108 is tightly weaved so as to achieve a substantially smooth surface on rubber sheet 104. In an embodiment, separator 108 is tightly plain weaved so as to achieve a substantially smooth surface on rubber sheet 104. In an embodiment, separator 108 has a thread count of at least 109×76 threads per inch (which is a tightly weaved separator) so as to achieve a substantially smooth surface on rubber sheet 104.

Figure 3:
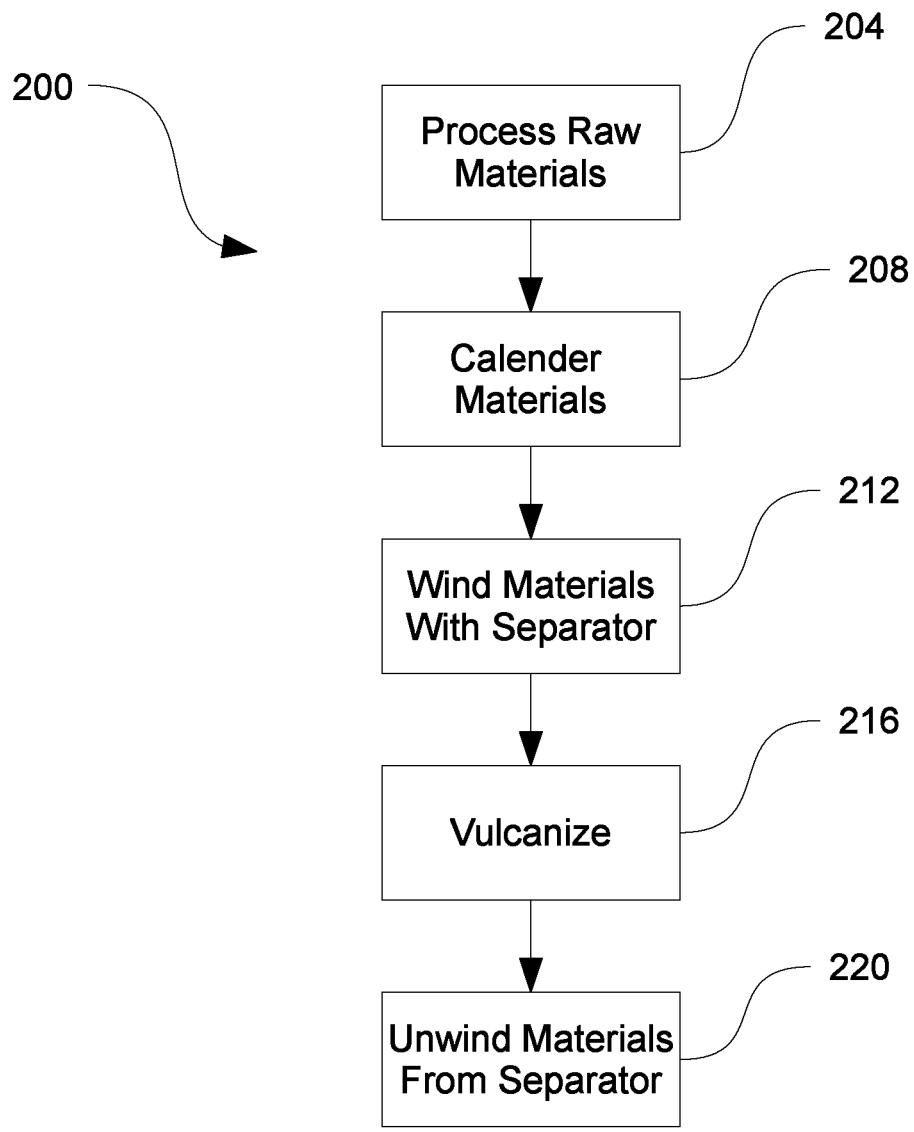
FIG. 3 is a process diagram of a method of making a substantially smooth, dust-agent free rubber product according to an embodiment of the present invention.

Turning now to FIG. 3, a method 200 of making a substantially smooth, dust free, rubber sheet is described. At step 204 raw materials are processed. In an embodiment processing raw materials can include, but is not limited to, mixing raw rubber material together, extruding and straining the raw materials, and testing the raw materials for qualities, such as viscosity, stress relaxation, scorch, and other qualities of the raw rubber materials.

At step 208, the raw materials are calendered. Calendering processes rubber by forcing the material softened by heat through typically two to five counter-rotating rollers. The resulting product has a thickness that is determined by the spacing between the rollers. In an embodiment, a four roll calendering system is used to thin the raw materials to the desired thickness, however, more or fewer rollers may be used. As is known in the art, the calendering system can include heated rollers so as to aid in the thinning of the raw materials.

At step 212, the calendered rubber sheet is wound onto a large roller with a separator sheet, such as one or more embodiments of separator 108 described herein, so as to keep the calenderized rubber sheet from sticking to itself as it is rolled onto the large roller. In an embodiment, the separator sheet and the calenderized rubber sheet are combined on a drum, such as drum 116 using a system, such as system 100 described herein.

At step 216, the large roller is placed into a vulcanization oven. In an embodiment, the large roller is placed into a hot air oven and is heated for a predetermined amount of time and at a predetermined temperature. In an embodiment, the large roller is heated for about 4 hours at about 140 to 150° C.

At step 220, the large roller is removed from the vulcanization oven and placed on a sheet removal device. In an embodiment, the sheet removal device can be substantially similar to system 100 only operating in reverse. In this embodiment, the separator and the vulcanized rubber sheet are unwound from the large roller, with the separator being rewound onto a roller, such as one of fabric rollers 148 and the vulcanized rubber sheet is wound onto its own roller for further processing. Notably, the vulcanized rubber sheet has a practically impressionless appearance due to the construction of the separator and post-vulcanization is no longer tacky.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A process for the manufacture of a substantially smooth, dust free, rubber sheet, comprising:
   calendering a rubber material into a rubber sheet;
   combining the rubber sheet on a drum with a separator such that layers of the separator separate layers of the rubber sheet, wherein the separator is a tightly weaved, low shrinkage, thermoplastic textile and wherein no dusting agent is applied to the rubber sheet;
   heating the combined rubber sheet and separator so as to vulcanize the rubber sheet; and
   separating the vulcanized rubber sheet from the separator,
   wherein the separator is plain weaved and has a thread count of at least 109×76 threads per square inch;
   wherein the separator is chemically treated with a silicone;
   wherein the separator is thermally stabilized after treatment with the silicone by heating the separator to above the temperature of vulcanizing prior to combining the separator with the rubber sheet; and
   wherein the thermoplastic material of the thermoplastic textile is selected from the group consisting of nylon and polyester.

* * * * *